United States Patent
Allen et al.

(10) Patent No.: US 9,386,261 B2
(45) Date of Patent: Jul. 5, 2016

(54) SYSTEM AND METHOD FOR TRANSMISSION, ONLINE EDITING, STORAGE AND RETRIEVAL, COLLABORATION AND SHARING OF DIGITAL MEDICAL VIDEO AND IMAGE DATA

(75) Inventors: Robert C. Allen, Santa Luz, CA (US); Steven W. Corey, Sausalito, CA (US); Mark S. McCoy, San Mateo, CA (US)

(73) Assignee: PhotoBaby, Inc., Del Mar, CA (US)

( * ) Notice: Subject to any disclaimer, the term of this patent is extended or adjusted under 35 U.S.C. 154(b) by 936 days.

(21) Appl. No.: 12/138,335

(22) Filed: Jun. 12, 2008

(65) Prior Publication Data
US 2008/0310816 A1    Dec. 18, 2008

Related U.S. Application Data

(60) Provisional application No. 60/944,311, filed on Jun. 15, 2007.

(51) Int. Cl.
| | | |
|---|---|---|
| H04N 5/272 | (2006.01) | |
| H04N 5/76 | (2006.01) | |
| A61B 8/00 | (2006.01) | |
| G11B 27/034 | (2006.01) | |
| G11B 27/036 | (2006.01) | |
| H04N 21/2743 | (2011.01) | |
| H04N 21/472 | (2011.01) | |
| H04N 5/765 | (2006.01) | |
| H04N 5/781 | (2006.01) | |
| H04N 5/85 | (2006.01) | |
| H04N 9/82 | (2006.01) | |

(52) U.S. Cl.
CPC *H04N 5/76* (2013.01); *A61B 8/468* (2013.01); *G11B 27/034* (2013.01); *G11B 27/036* (2013.01); *H04N 21/2743* (2013.01); *H04N 21/47205* (2013.01); *H04N 5/765* (2013.01); *H04N 5/781* (2013.01); *H04N 5/85* (2013.01); *H04N 9/8205* (2013.01)

(58) Field of Classification Search
USPC .......................................................... 382/128
See application file for complete search history.

(56) References Cited

U.S. PATENT DOCUMENTS

| | | | | | |
|---|---|---|---|---|---|
| 1,294,249 | A | * | 2/1919 | Eckels | ............................ 352/55 |
| 2,065,028 | A | * | 12/1936 | Rufle et al. | ...................... 352/90 |

(Continued)

OTHER PUBLICATIONS

Shutterfly ("Put Your Pictures on the Big Screen With Shutterfly's Photoshow DVD", Press Release dated Aug. 2005).*

(Continued)

*Primary Examiner* — Clayton E Laballe
*Assistant Examiner* — Leon W Rhodes, Jr.
(74) *Attorney, Agent, or Firm* — Knobbe Martens Olson & Bear LLP

(57) ABSTRACT

Medical video clips are accepted, customized, and a video or image is created from the video clip. In one embodiment, the video clip is a prenatal ultrasound and the customization includes specifying biographical information for the baby and selecting border and audio. In another embodiment, video clips or images are from medical devices including CAT scans, MRIs, X-Ray systems, ultrasounds or standard digital video or still image capture devices used for procedural documentation purposes. The customization includes annotating the video clips in order to share and collaborate. Video editing and sharing is typically done via an Internet appliance.

20 Claims, 8 Drawing Sheets

(56) References Cited

U.S. PATENT DOCUMENTS

| | | | |
|---|---|---|---|
| 5,666,215 A * | 9/1997 | Fredlund | H04N 19/60 358/487 |
| 6,285,985 B1 * | 9/2001 | Horstmann | 705/14.61 |
| 6,349,143 B1 | 2/2002 | Hastings et al. | |
| 6,406,428 B1 * | 6/2002 | Mittelstaedt | A61B 8/14 600/437 |
| 6,829,378 B2 * | 12/2004 | DiFilippo et al. | 382/128 |
| 7,457,672 B2 * | 11/2008 | Katsman et al. | 700/17 |
| 2002/0120757 A1 * | 8/2002 | Sutherland | G06F 21/604 709/229 |
| 2003/0046150 A1 * | 3/2003 | Ader | G06Q 20/123 705/14.67 |
| 2003/0206646 A1 * | 11/2003 | Brackett | 382/128 |
| 2004/0205138 A1 * | 10/2004 | Friedman | G06Q 30/02 709/206 |
| 2004/0250205 A1 * | 12/2004 | Conning | 715/517 |
| 2004/0267116 A1 | 12/2004 | Flood et al. | |
| 2005/0165627 A1 * | 7/2005 | Fotsch et al. | 705/3 |
| 2005/0280651 A1 * | 12/2005 | Geddes | G11B 27/34 345/547 |
| 2006/0122482 A1 | 6/2006 | Mariotti et al. | |
| 2006/0259588 A1 * | 11/2006 | Lerman et al. | 709/219 |
| 2007/0118801 A1 | 5/2007 | Harshbarger et al. | |
| 2007/0277108 A1 * | 11/2007 | Orgill | G11B 27/034 715/730 |
| 2008/0006282 A1 * | 1/2008 | Sukovic et al. | 128/922 |
| 2008/0279437 A1 * | 11/2008 | Hendricks et al. | 382/131 |
| 2009/0136133 A1 * | 5/2009 | McGann | 382/176 |

OTHER PUBLICATIONS

EZedia ("EZedia Plug-in Bundle for iMovie Announced at Apple Expo Paris", News Release dated Sep. 2002, retrieved from MacTech.com).*

Ultrasound Advantage ("Business Will Offer Women Ultrasound Photos of Their Unborn Babies", RedOrbit.com posting of Fort Wayne News-Sentinel article, dated Apr. 2005).*

Lubell ("The Womb as Photo Studio", NY Times article dated Sep. 2004).*

"Here's Looking at You" (Orlando Sentinel [Orlando, Fla] Jul. 6, 2000: E2).*

"Edmond Firm" (Journal Record [Oklahoma City, Okla] Jan. 22, 2001: 1).*

"Kodak Shows the Demise" (.Rochester Democrat and Chronicle [Rochester, N.Y] Jun. 28, 2000: D.10).*

"Kodak will Offer" (Austin American Statesman [Austin, Tex] Feb. 21, 1997: D.8).*

Notification of Transmittal of the International Search Report and the Written Opinion of the International Searching Authority dated Aug. 7, 2008 for corresponding International Patent Application No. PCT/US08/66921, 7 pages.

\* cited by examiner

SYSTEM AND METHOD FOR TRANSMISSION, ONLINE EDITING, STORAGE AND RETRIEVAL, COLLABORATION AND SHARING OF DIGITAL MEDICAL VIDEO AND IMAGE DATA

CROSS REFERENCE TO RELATED APPLICATIONS

This application claims priority from our provisional patent application No. 60/944,311 filed Jun. 15, 2007 and titled "PhotoBaby Version 1.0".

FIELD OF THE INVENTION

The present invention generally relates to digital and digitized video and image composition and, more specifically, to creating edited videos or images from medical procedures such as fetal ultrasounds, MRIs, CAT scans, or other film or digitally captured medical procedures.

BACKGROUND OF THE INVENTION

The economics of health care has changed dramatically of the last 10 to 15 years. Doctors are looking for more sophisticated and efficient ways to edit, manage, and store digital medical media as well as additional revenue sources to supplement the fees earned on providing healthcare services. In addition, healthcare providers are looking for ways to distinguish themselves from their competitors. As an example, there are approximately 60,000 Obstetricians in the United States. Many of them are looking for a competitive edge.

Additionally, medical practitioners are increasingly utilizing medical digital video and image capture in the course of providing their healthcare services. Some of the problems that arise are inefficiencies in the sharing and distribution of this information. Furthermore, the tools for collaboration are rudimentary at best. There is a need to facilitate enhanced sharing, collaboration and training opportunities among doctors and other medical practitioners in both practice and training or educational environments.

With the creation of a new generation of medical digital video and image capture technologies utilized for both diagnostic imaging and procedural documentation purposes, there is a need for a new tool to facilitate transmission, online editing, storage and retrieval, collaboration and sharing of this digital medical video and image data to create new efficiencies. For example, the new ultrasound machines can produce high-resolution three and four dimensional digital videos and images of the fetus and provide their patients with a unique prenatal view of their baby. The current practice is to give the patients a hard copy of the video and/or still images taken from the exam that the patients proudly share among family and friends. This practice necessitates an interruption to the workflow within the practice to burn a DVD or CD or provide a VHS tape to the patient and presents the video and/or images in an unedited, non-personalized, medical format only.

BRIEF SUMMARY OF THE INVENTION

The present invention provides a solution for doctors to incorporate best practices in a medical procedure to efficiently capture medical data, securely transmit it to an online service where based on log-in credentials the medical data is associated with a medical practitioner and/or a patient. The digital media is then securely accessed online and by way of a wizard driven graphic user interface manipulated/edited to better or functionally illustrate or communicate for an intended purpose, and additionally, is associated with medical and/or non-medical meta-data. Intended purposes include, but are not limited to, keepsake or entertainment, professional collaboration, sharing and training.

The online service component will preferably integrate with industry standard medical integration technologies such as The Digital Imaging and Communications in Medicine (DICOM) standard for purposes of compliance and sharing amongst medical practitioners bound by physician/patient confidentiality and obligated to comply with all HIPPA practice standards and regulations.

With the advent of a new generation of medical digital video and image capture technologies utilized for both diagnostic imaging and procedural documentation purposes the idea of giving the patients the opportunity to have a digital video or image copy of all or part of a medical procedure is an exciting prospect. This product could not only provide the medical practitioner with an additional source of revenue, but also serve as a unique marketing differentiator among the consumer/patients. Additionally, it serves as a highly efficient means of collaboration or sharing with other medical professionals which given the highly specialized nature of the medical industry, could by virtue of increased exposure through interaction, lead to improved patient referral rates from other practitioners.

DETAILED DESCRIPTION OF THE INVENTION

Figure 1:
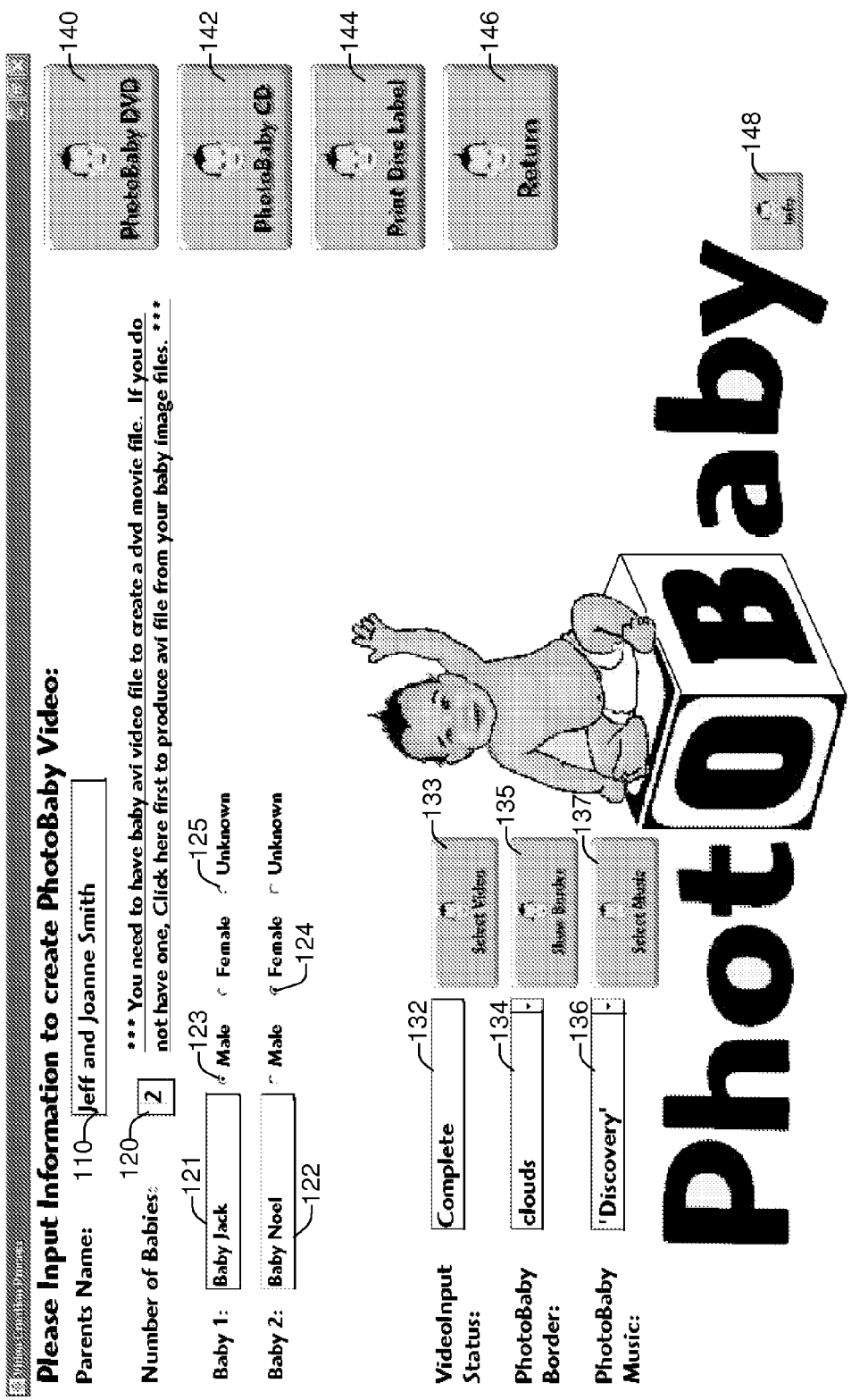
FIG. 1 is a diagram illustrating a customization screen, in accordance with one embodiment of the present invention.

The economics of health care has changed dramatically of the last 10 to 15 years. Doctors are looking for more sophisticated and efficient ways to edit, manage, and store digital medical media as well as additional revenue sources to supplement the fees earned on providing healthcare services. In addition, healthcare providers are looking for ways to distinguish themselves from their competitors. As an example, there are approximately 60,000 Obstetricians in the United States. Many of them are looking for a competitive edge. By enabling the use of the present invention by these medical professionals as an adjunct to a medically necessary procedure we hope that this might reduce the number of ultrasounds that are being done purely for entertainment or keepsake purposes.

Additionally, the scope of the present invention aptly applies to a spectrum of medical practitioners who routinely utilize medical digital video and image capture in the course of providing their healthcare services. As such, the efficiencies represented by way of the present invention's implementation into a medical practice will likely lead to additional revenue sources for the practice and entertainment or keepsake value-added products for the patient consumer that are of no consequence in terms of safety, medical ethics, or work flow for the doctor. Furthermore, the same efficiencies represented within the scope of the present invention will likely facilitate enhanced sharing, collaboration and training opportunities among doctors and other medical practitioners in both practice and training or educational environments.

The PhotOBaby system is intended to be used by obstetrical office to produce a movie of a digital file produced by an ultrasound machine. The targeted obstetrical office will typically have an ultrasound machine that can produce 3 dimensional images of the fetus, but this is not a requirement. Also, movies from ultrasounds from other sources may also be utilized. Any ultrasound video in a compatible format can be used to produce the movie. After an examination is completed, a technician will typically copy a selected video clip from the ultrasound machine. This video clip will preferably, but not necessarily, have an upper time limit that has not yet been determined. Probably the maximum clip length will be in the four minute range. However, other lengths of clip are also within the scope of this invention.

In one embodiment, the video clip will be copied onto a CD, DVD, etc. The CD will be placed into a CD drive on the computer that has the software. The user of the software will then fill in a form with answers that include number of babies, parents' last name, and sex of babies if known. The parents will also choose the music and the border that they wish to incorporate into the video. The parents will also select whether they wish the movie to be created on a CD or DVD. Once the selection process has been completed the technician will press a button to continue the process. The software will then copy the video clip from the CD in the CD drive and process it. Once the movie creation process has been completed the user will be prompted to place a blank writeable CD or DVD into the drive and the movie will be copied onto the media. We may wish to make the DVD creation capability optional to provide the obstetrical office with pricing flexibility.

In another embodiment, the video clip will be uploaded to a web based application from the physician's office or from the office where an ultrasound was created. As an alternative, the patient or parents may upload a video clip from another source. The patient or parents would then typically be given a code or userid/password for accessing the video clip. They could then choose the music and border that they wished to incorporate into the video. They may pick from selections available on the site, or they may upload their own music and/or border. They may also upload an introductory page and/or other video to play before and/or after the video clip. If they don't upload their own introductory page, they would typically be asked to fill in important identifying information for the video clip, including, for example, names of the parents, number of babies, their sex (if known), their names (if known), date of ultrasound, gestational age of the baby, etc.

After a video is created from the video clip, it can be downloaded over the web to a user's computer where it can be stored on their hard drive, shared across the Internet, or burned onto a CD or DVD. It may also be shared from the PhotoBaby site. In that case, the expectant parents or others using the system may distribute keys or codes to other interested parties, such as family and friends, so that they can access the PhotoBaby web site and view or download the video from there.

The target purchaser of the software in the first embodiment is the obstetrician or business manager of an obstetrical office interested in providing additional services to their patients. The target user will probably be either the ultrasound technician performing the ultrasound and/or an office staff person. The expectant parents will be the purchaser of the output of the software, but they are considered customers of the obstetrical office.

In the web based second embodiment disclosed above, the target market includes the patient, expectant parents, grandparents, and other interested parties. They would typically be the parties paying for the service. The obstetrical office or ultrasound laboratory would typically upload a video clip of ultrasounds as a service for the benefit of their patients, and could be rewarded if and when the patients, parents, etc. utilize the web based system. Alternatively, they could charge for the uploading.

As an alternative or additional revenue model, the web site may include paid advertisements. For example, baby products may be displayed in order to entice new parents into their purchase. Advertisers could pay for mere placement of advertising, for page views, or click throughs. This list is not exhaustive, since advertising and revenue generation over the Internet is an evolving technology, and other types of revenue generation are also within the scope of this invention.

The product has a relationship with the ultrasound machine that produces the video that is to be processed by the software. This product also has a relationship to industry standard computer CD drives and DVD players that will read and display the movies created by the software.

FIG. 1 is a diagram illustrating a customization screen, in accordance with one embodiment of the present invention. The customization screen provides for input of the parents' names 110 and number of babies expected 120. From the number of babies expected, a corresponding number of baby entries are opened up. For each baby, a name and sex (if known) are specified. In this example, two babies are shown. The first baby 121, "Baby Jack", is identified as "Male" 123. The second baby 122, "Baby Noel", is identified as "Female" 124. There is also a selection for "Unknown" 125 if the baby's sex is not known yet. In this embodiment, radio buttons are used to select the sex of a baby. Other alternatives are also within the scope of this invention.

Below the area where the baby or babies are identified is an area that contains video customization options. The first selection is for the status of the video clip to be used for this video. There is a "Video Input Status" indicator 132 which indicates whether or not a video clip has been selected and uploaded or downloaded, as appropriate. Next to this is a "Select Video" button 133 which, when pressed, brings up a screen (not shown) that provides for the selection, uploading, or downloading of a video clip. In one embodiment, this will be done in advance by the doctor's office. Below the Video Input Status indicator 132 is a Border Selection status box 134 showing the selection for the border to be placed around the video clip when creating the video. In one embodiment, the users will select the border from a pull down menu. In another embodiment, the user will be given the choice of either selecting a preloaded border or uploading his or her own border. This can be accomplished by selecting the "Show Border" or "Select Border" button 135. Below the Border status indicator and (possibly) pull-down menu 134 is a Music Selection status box 136. In one embodiment, the user selects music from a pull-down menu. In another embodiment, the user is given the choice of selecting the music from a preloaded library of music clips or uploading his or her own selection of music. To the right of the Music Selection status box 136 is a "Play Music" or "Select Music" button 137. In the later case, a menu or page will be launched that allows the user to upload audio clips, to listen to what clips are available, and to select one audio clip to include with the video to be created.

Also, available on the right side of this screen are buttons utilized to create CDs and DVDs. In this example, there are buttons to: create a DVD 140, create a CD 142, label a CD or DVD 144, and to Return 146 to a higher level of menu. There is also an "Info" 148 button available for getting more information. In another embodiment, there is also a "Help" button (not shown) available for getting help, should that be necessary. Other buttons and boxes are also within the scope of this invention. For example, users may be given the option of specifying a custom introductory screen or a finale screen. Also, this screen may provide advertising for review by the users, and those advertisements may have links to web pages for the advertisers.

Figure 2:
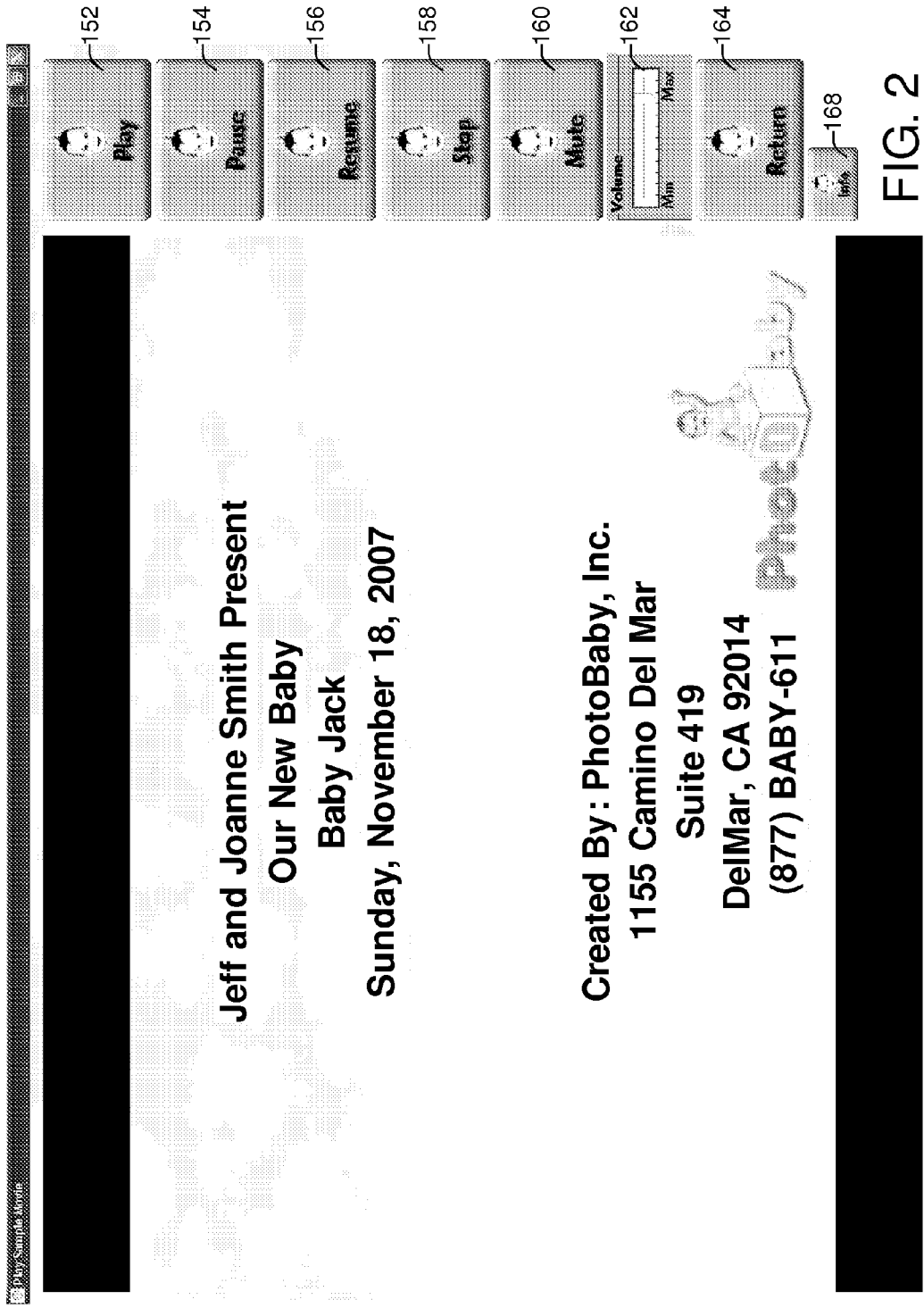
FIG. 2 is a diagram illustrating a introductory screen, in accordance with one embodiment of the present invention.

FIG. 2 is a diagram illustrating a introductory screen, in accordance with one embodiment of the present invention. A screen like this is typically presented before the video clip when the video is played. In this example, the introductory screen contains much of the information from the customization screen (see FIG. 1 above), including names of the parents, their baby or babies, and the date created or when the video clip was taken. This screen also shows the company that provided the system for creating the video.

Along the right side of the screen are buttons to control the running of the video. In this embodiment, the following buttons are shown: "Play" 152 for playing the video, "Pause" 154 for pausing the video, "Resume" 156 for resuming playing the video, "Stop" 158 for stopping the playing of the video, "Mute" 160 for muting and unmuting the audio. There is also an audio Volume control 162 for controlling the volume level of the audio. These are followed by a "Return" button 164 and an "Info" button 168. Other buttons and controls may also be included, and other methods utilized to control the play of the video, including using the standard Windows or Mac video play controls.

Figure 3:
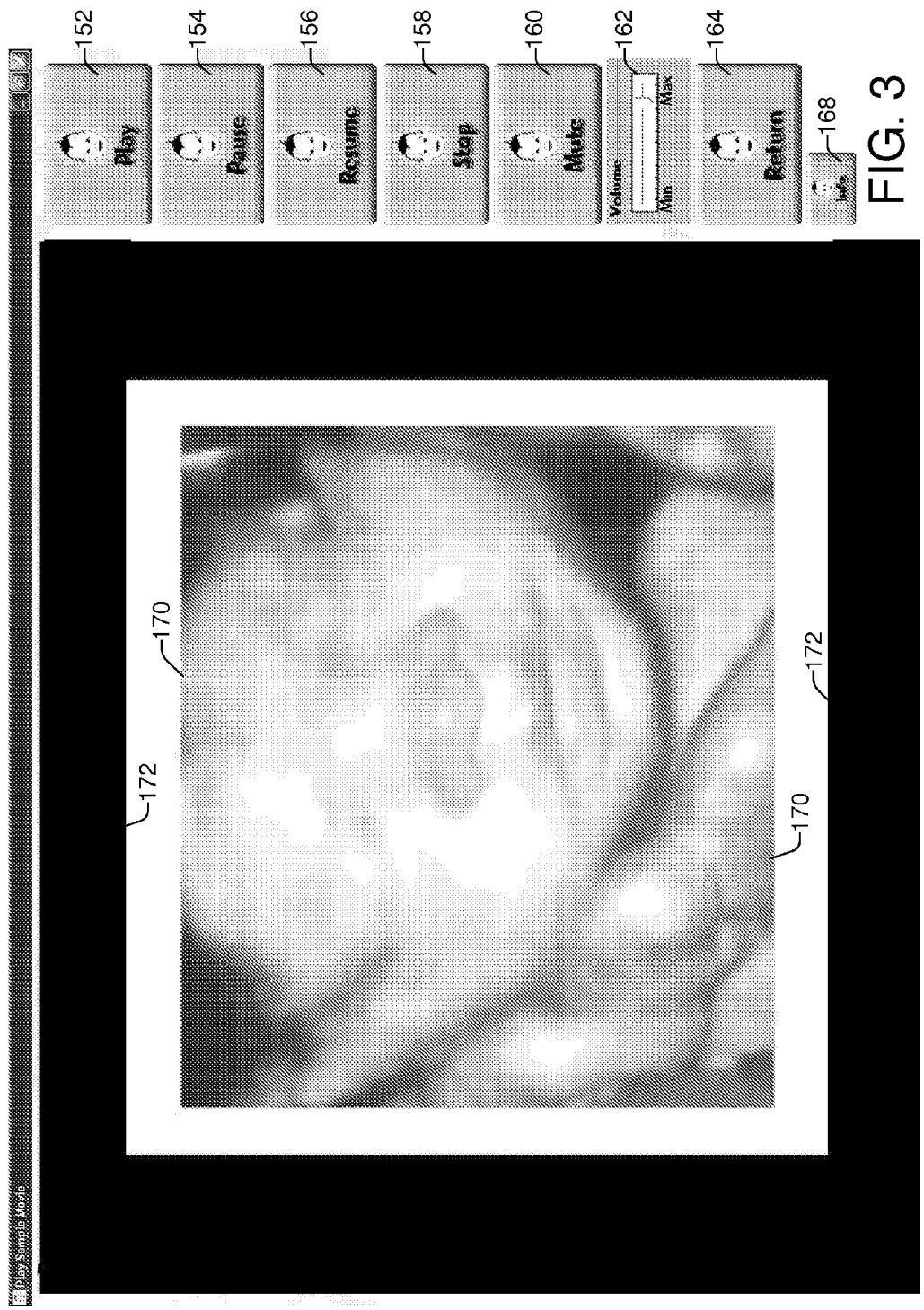
FIG. 3 is a diagram illustrating an video play screen, in accordance with one embodiment of the present invention.

FIG. 3 is a diagram illustrating an video play screen, in accordance with one embodiment of the present invention. This screen is similar to the introductory screen shown in FIG. 2, except that instead of customized biographical information, the actual video clip 170 (e.g. recording of an ultrasound) is played within a border 172. An ultrasound of a fetus is shown in this example. The control buttons to the right are identical to those shown for the introductory page shown in FIG. 2. The border shown is typically selected on the customization screen shown in FIG. 1. Similarly, the audio in the video is typically also selected from that customization screen.

Figure 4:
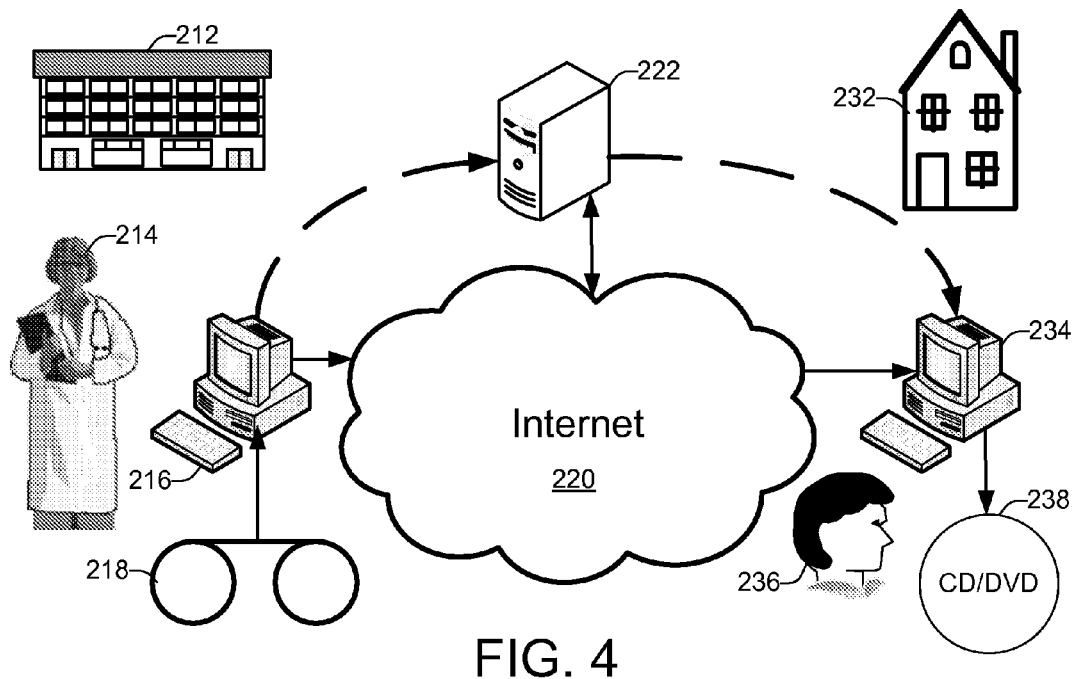
FIG. 4 is a diagram illustrating components of a web based embodiment of the present invention.

FIG. 4 is a diagram illustrating components of a web based embodiment of the present invention. In this exemplary embodiment, a doctor or technician 214 at a medical facility 212, such as a doctor's office, performs a procedure or test that results in a video clip 218. The video clip 218 is uploaded to a computer 216, and then to a server 222 across the Internet 220. In the example above, the test is an ultrasound of an expectant mother and the video clip shows the progression of the ultrasound as the monitor is moved around the mother's belly. Some testing equipment is already connected to a network and the video clip can be uploaded from there. Alternatively, it may be converted to another format before such an upload. In other instances, the results of the test or procedure are not digitized or not available for upload. In those instances, it may be necessary for the computer 216 to capture the video clip. This can be done for example, utilizing S-Video connectors. Indeed, this technique can be utilized to capture audio from a VCR tape.

The customization and play software will typically be installed on a server 222 available to users across the Internet 220. This will typically be the same server 222 to which the video clip 218 had been uploaded. Users 236 sitting at their computers 234 at their homes 232 can create videos from the video clips 218 previously uploaded to the server 222. They can download them to their computer 234, to a CD, DVD, or Flash card 238, or send an invitation to view the video on the server 222 to their family and friends.

Figure 5:
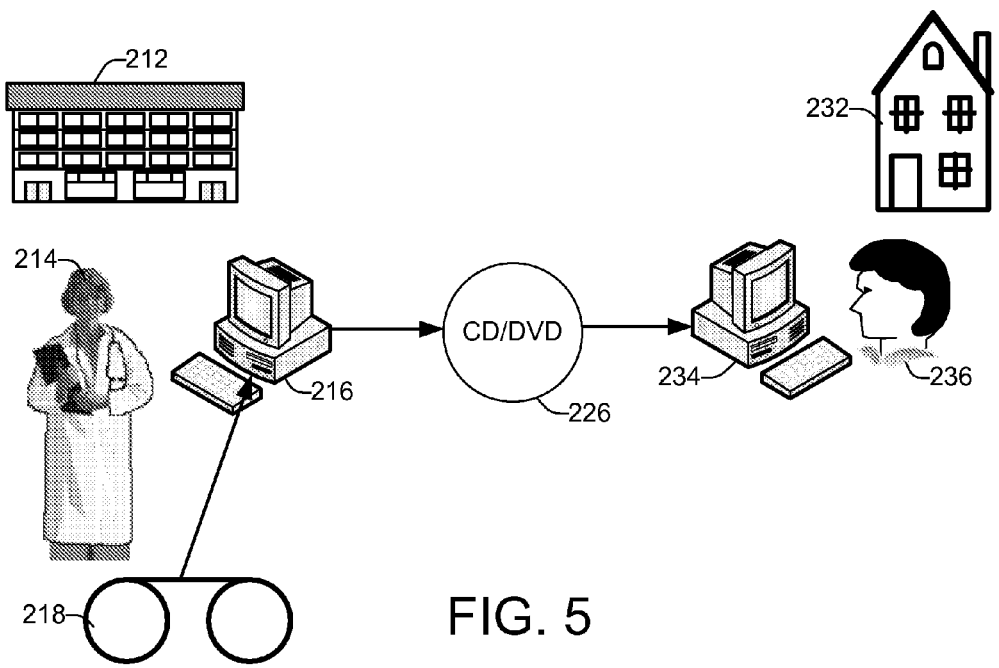
FIG. 5 is a diagram illustrating components of a kiosk based embodiment of the present invention.

FIG. 5 is a diagram illustrating components of a kiosk based embodiment of the present invention. In this exemplary embodiment, a doctor or technician 214 at a medical facility 212, such as a doctor's office, performs a procedure or test that results in a video clip 218. The video clip 218 is uploaded to a computer 216. In the example above, the test is an ultrasound of an expectant mother and the video clip shows the progression of the ultrasound as the monitor is moved around the mother's belly. Some testing equipment is already connected to a network and the video clip can be uploaded from there. Alternatively, it may be converted to another format before such an upload. In other instances, the results of the test or procedure are not digitized or not available for upload. In those instances, it may be necessary for the computer 216 to capture the video clip. This can be done for example, utilizing S-Video connectors.

The user will then customize and create the video from the video clip 218 utilizing the computer 216 at the doctor's office 212. When complete, the video is downloaded to a CD, DVD, Flash card, etc. 226, which the user 236 can take home 232 and play on his own computer 234. He can then duplicate the CD, DVD, Flash card, etc. for his friends and family, or email the video to them.

Figure 6:
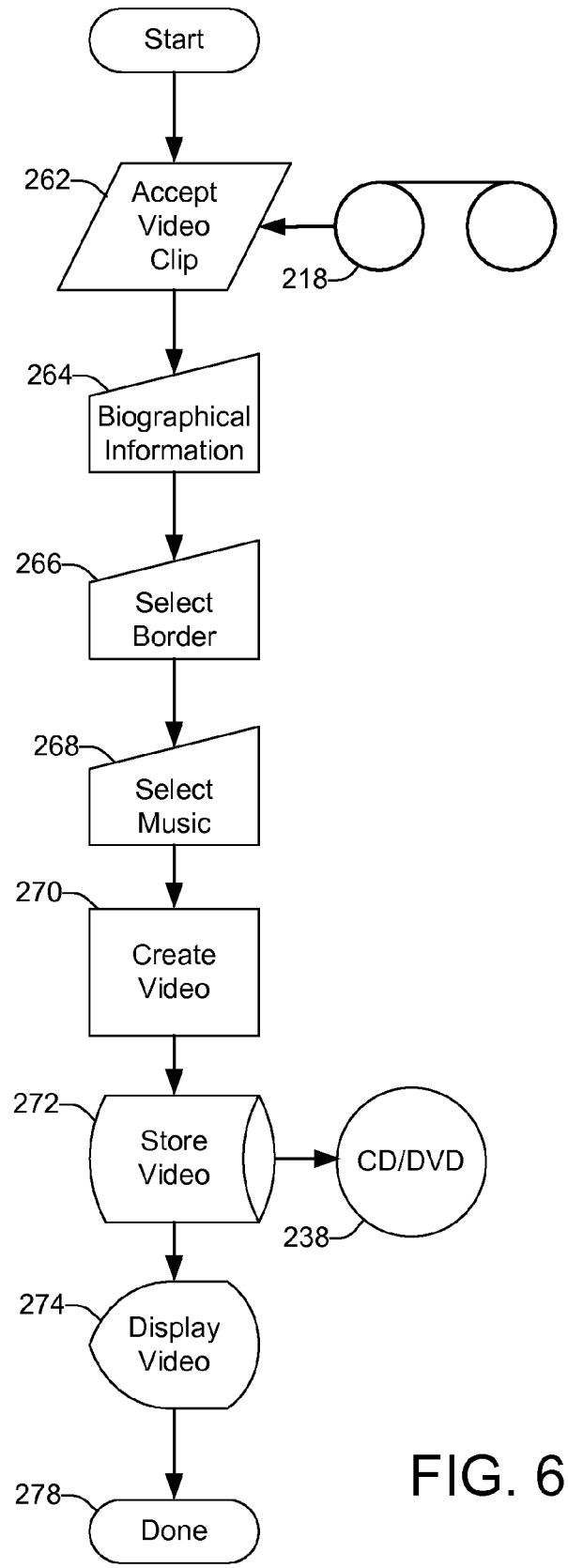
FIG. 6 is a flowchart illustrating exemplary operation of one embodiment of the present invention.

FIG. 6 is a flowchart illustrating exemplary operation of one embodiment of the present invention. It starts by accepting 262 a video clip 218. In the example used above, the video clip is a video of an ultrasound of a human fetus. In many cases, a video clip of the test or procedure is in digital form usable for making the video, and it can be used directly. In other instances, it has to be captured, for example, using S-Video capture. Once the video clip has been accepted, step 262, and uploaded, biographical information is accepted, step 264, from the user (see FIG. 1). Also, from the customization menu or screen (see FIG. 1), a border is selected, step 266, and music or audio selected, step 268, and uploaded if necessary. The video is then created, step 270, from the customization information, selected border, and selected music. The created video is stored, step 272, and optionally written to auxiliary storage, such as CD, DVD, Fash, etc. 226, 238. The video may be displayed, step 274, utilizing, for example, the controls shown in FIGS. 2 and 3. The method is then complete.

Figure 7:
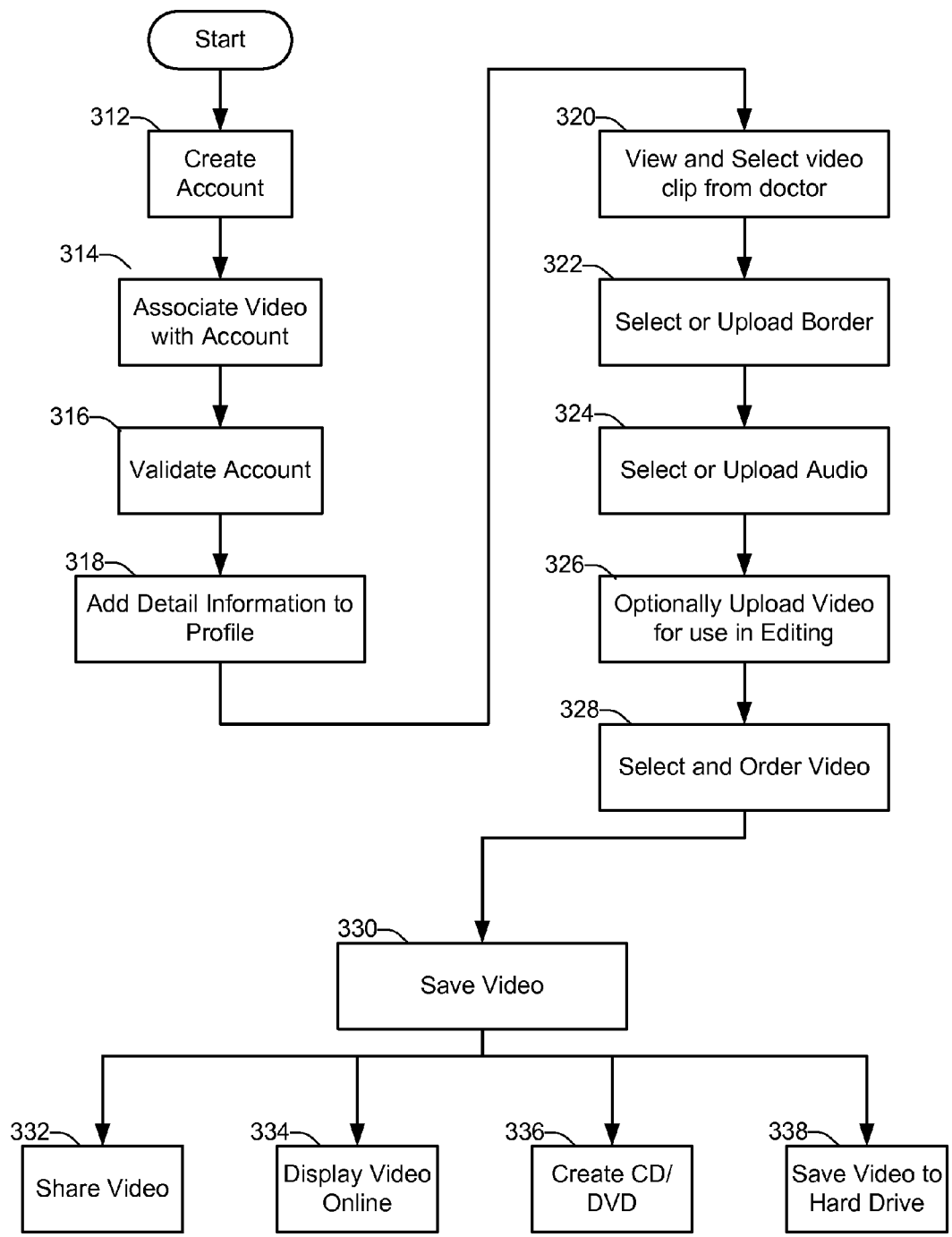
FIG. 7 is a flowchart illustrating exemplary operation of a doctor/patient embodiment of the present invention.

FIG. 7 is a flowchart illustrating exemplary operation of a doctor/patient embodiment of the present invention. An account is created for a patient, step 312. Video, such as an ultrasound, is associated with the patient and account, step 314. The account is validated, step 316. Detail information is added to the profile, typically by the patient, step 318. A video clip is viewed and selected, typically by the patient, step 320. A border is selected or uploaded, step 322. Audio is selected or uploaded, step 324. Optionally, additional video is uploaded for use in editing the resulting video, step 326. The video is created. A video is then selected and ordered, step 328. The video is saved, step 330. This could entail sharing the video online, step 332, displaying the video, step 334, creating a CD/DVD containing the video, step 336, and/or storing the video to a hard drive, step 338.

Another embodiment of the present invention involves sharing of videos and other medical information. When a doctor is going to collaborate with a doctor directly over the web, they will do this by specifying the doctor's email they want to collaborate with. This will generate a request sent to the collaborating doctor. If the doctor already has an account, they are sent a request to collaborate email. The collaborating doctor then logs into the service and they will see a listing of patients that they have been provisioned the ability to collaborate on. The doctor then selects the patient and they can see the meta data and video and can markup the video or make comments on the data. The only difference between this and a doctor that does not have an account already setup is that they will be given a default login and password and when they login they will be prompted to change their password and complete their profile.

The second method of collaboration is integration to existing technologies. The sending doctor specifies the means of collaboration e.g. DICOM server. Each method of integration has its own set of parameters and the doctor will submit the parameters required to reach the receiving doctor's collaboration technology. The meta data and video is then sent via the service to the receiving doctor's collaboration technology.

Once the Doctors access the video or images they will be able to add annotation and mark-up as well as audio or voice-over. The tools will be different than in the "keepsake" version, but the system and process is essentially the same.

Figure 8:
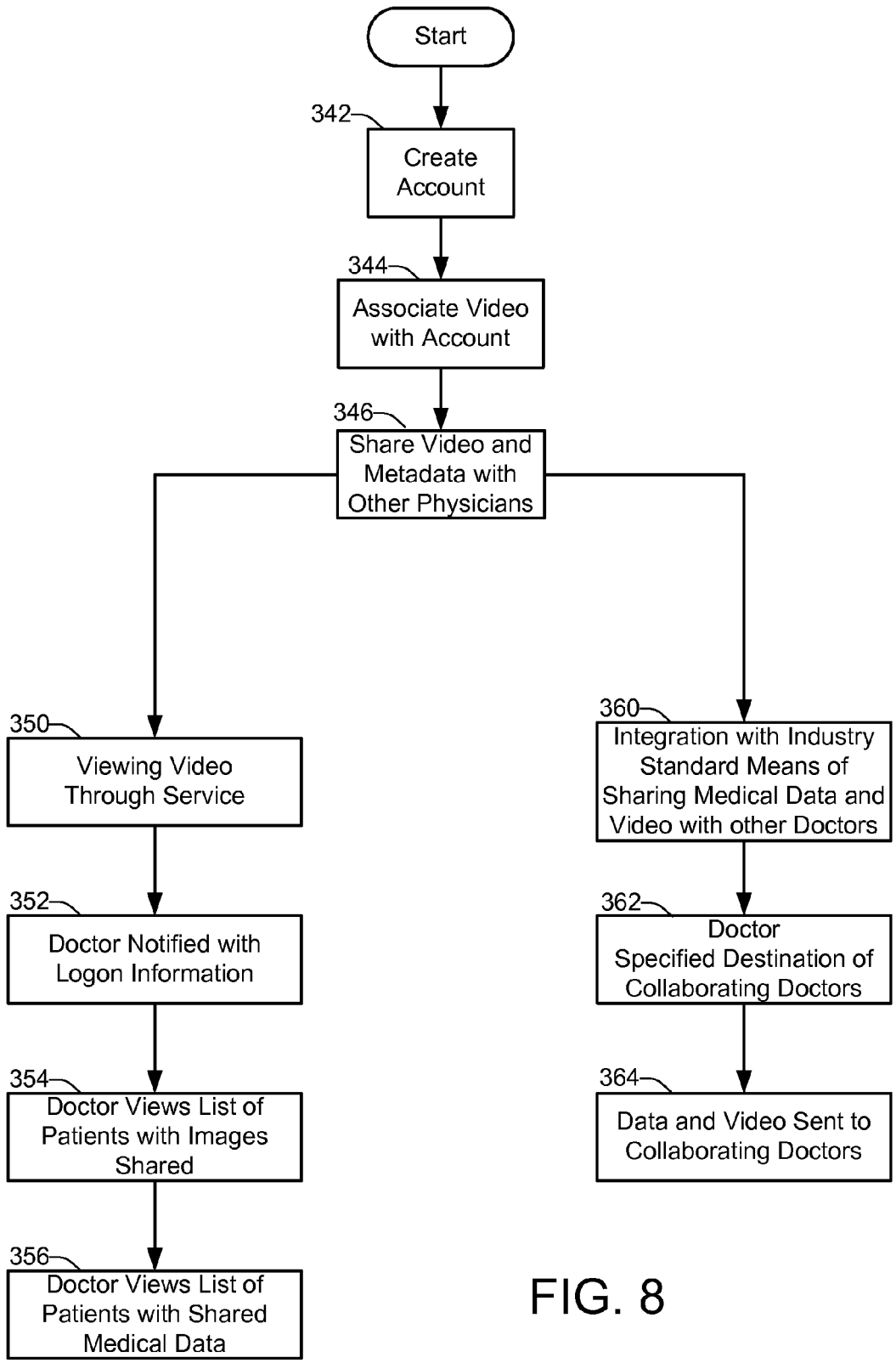
FIG. 8 is a flowchart illustrating exemplary operation of a doctor/doctor embodiment of the present invention.

FIG. 8 is a flowchart illustrating exemplary operation of a doctor/doctor embodiment of the present invention. An account is created, if necessary, step 342. A video is associated with the account, step 344. The video is shared with other doctors and medical professionals, step 346. Two different paths are shown here. If Viewing Data through a service, step 350, the second doctor is notified of his login, step 352, he logs in with that log in, views a list of patients with shared video, step 354, and a list of patients with shared medical data, step 356. On the other hand, if the sharing is integrated with industry standard means of sharing medical data and video with other physicians, step 360, the destination of collaborating doctors is specified, step 362, and the data and video are sent to the collaborating doctors, step 364.

Figure 9:
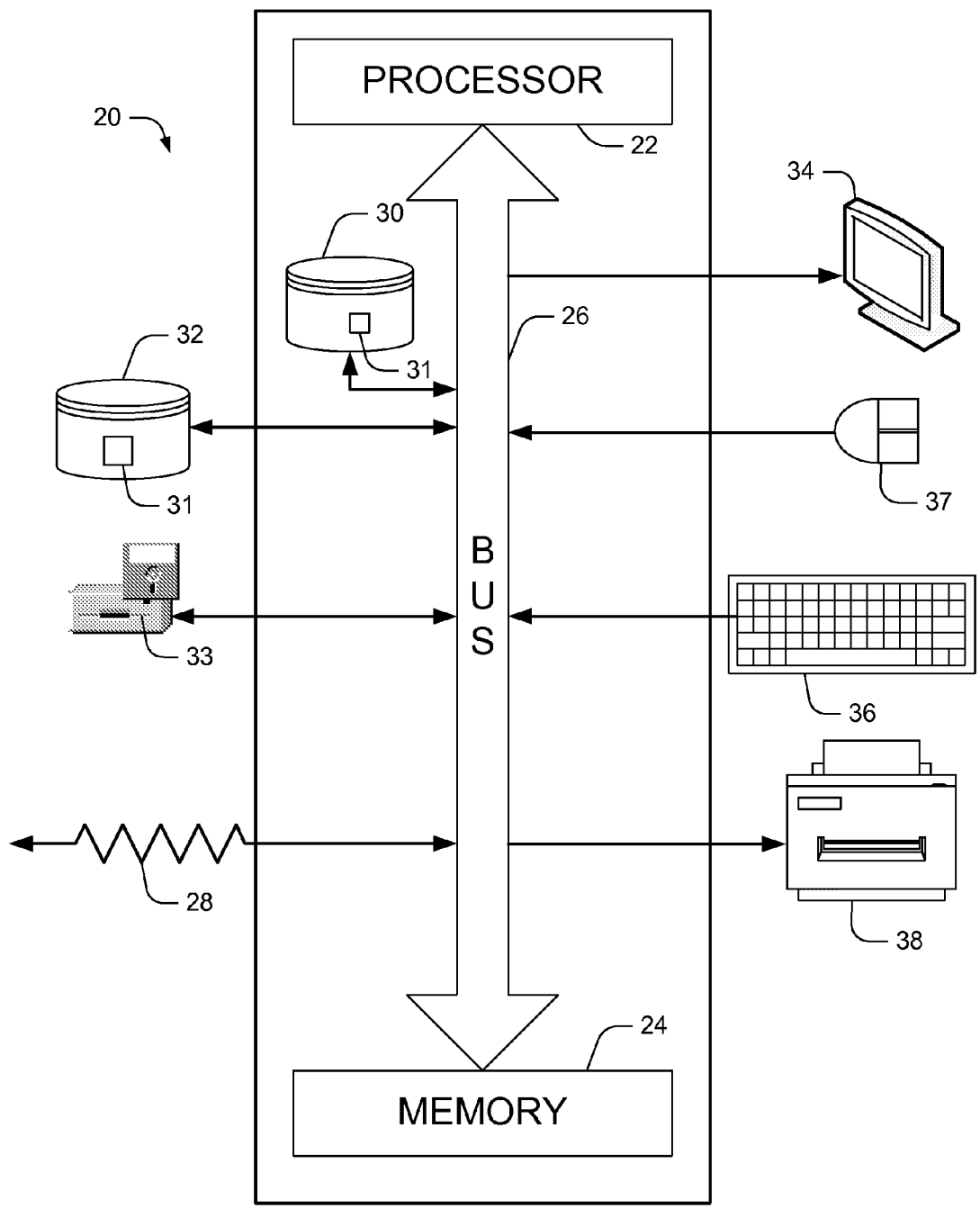
FIG. 9 is a block diagram illustrating a General Purpose Computer.

FIG. 9 is a block diagram illustrating a General Purpose Computer 20. The General Purpose Computer 20 has a Computer Processor 22 (CPU), and Memory 24, connected by a Bus 26. Memory 24 is a relatively high speed machine readable medium and includes Volatile Memories such as DRAM, and SRAM, and Non-Volatile Memories such as, ROM, FLASH, EPROM, EEPROM, and bubble memory. Also connected to the Bus are Secondary Storage 30, External Storage 32, output devices such as a monitor 34, input devices such as a keyboard 36 with a mouse 37, and printers 38. Secondary Storage 30 includes machine-readable media such as hard disk drives, magnetic drum, and bubble memory. External Storage 32 includes machine-readable media such as floppy disks, removable hard drives, magnetic tape, CD-ROM, and even other computers, possibly connected via a communications line 28. The distinction drawn here between Secondary Storage 30 and External Storage 32 is primarily for convenience in describing the invention. As such, it should be appreciated that there is substantial functional overlap between these elements. Computer software such test programs, operating systems, and user programs can be stored in a Computer Software Storage Medium, such as memory 24, Secondary Storage 30, and External Storage 32. Executable versions of computer software 33, such as that utilized to implement the embodiments shown above can be read from a Non-Volatile Storage Medium such as External Storage 32, Secondary Storage 30, and Non-Volatile Memory and loaded for execution directly into Volatile Memory, executed directly out of Non-Volatile Memory, or stored on the Secondary Storage 30 prior to loading into Volatile Memory for execution.

Those skilled in the art will recognize that modifications and variations can be made without departing from the spirit of the invention. Therefore, it is intended that this invention encompass all such variations and modifications as fall within the scope of the appended claims.

What is claimed is:

1. A method of customizing a source set of fetal ultrasound image or video files, comprising:
   providing an interface to a user for accessing a DICOM server from a user's device over a data network;
   receiving at the DICOM server a source set of fetal ultrasound image or fetal ultrasound video files in a DICOM format from an ultrasound equipment coupled to the data network, the DICOM server comprising a processor and a memory that stores a user's credentials and associated images or video files, wherein the processor is configured to:
   provide the user access to the source set of image or video files on the DICOM server in response to receiving and validating a username and password from the user over the data network;
   select one or more image or video files from the source set of image or video files based on at least one of a user input or a medical office input;
   prompt the user to select a plurality of different categories of customization information to accompany the one or more selected image or video files;
   prompt the user to enter identifying information into the server;
   receive a selection of customization information, including one or more of music, a border, and identifying information, from the user;
   create a customized video based on the selected one or more image or video files; and
   format the customized video based on the user entered customization and identifying information.

2. The method of claim 1, wherein providing the user access across the data network to the source set of image or video files includes providing access to at least one ultrasound video clip and an ultrasound image.

3. The method of claim 2, wherein the processor is further configured to:
   accept meta-data from the user across the data network; and
   append the meta-data to the customized video.

4. The method of claim 1, wherein the processor is further configured to provide the customized video for download to the user's device across the data network.

5. The method of claim 1, wherein the processor configured to receive the selection of customization information of one or more of a border and music to accompany the image or video files comprises the processor being configured to:
   prompt the user to select between a) uploading to the DICOM server a choice of one or more of a border and music to accompany the image or video files and b) selecting from choices presented by the server of one or more of a border and music to accompany the image or video files, wherein
   if the user selected to upload a choice of one or more of a border and music, accepting such an upload; and if the user selected from choices presented by the server of one or more of a border and music, accepting the selection made by the user.

6. The method of claim 1, wherein the processor is further configured to:
prompt the user to upload text to append to the image or video files;
accept text information uploaded by the user in response to the prompt; and
create the customized video including the text information.

7. The method of claim 1, wherein the identifying information includes biographical information about a baby and at least one of its parents.

8. The method of claim 1, wherein the processor is further configured to:
accept at least one annotations, an audio overlay, and a diagram from the user across the data network; and
append the at least one annotation, audio overlay, and diagram to the customized video.

9. The method of claim 1, wherein the processor is further configured to provide the customized video for download or viewing by other users across the data network based on verification of the other users.

10. The method of claim 1, wherein processor is further configured to select one or more advertisements to be displayed during creation of the customized video.

11. An apparatus for customizing a source set of fetal ultrasound image or fetal ultrasound video files, comprising:
a DICOM server comprising a memory for storing user credentials and associated images or video files and a processor, the processor configured to:
provide an interface for user access from a user's device over a data network;
receive a source set of fetal ultrasound image or fetal ultrasound video files in a DICOM format from a network connected ultrasound equipment via the data network;
provide the user access to the source set of image or video files in the memory in response to receiving and validating a user's credentials over the data network;
select one or more image or video files from the source set of image or video files based on at least one of a user input or a medical office input;
prompt the user to select and provide a plurality of different categories of customization information to accompany the one or more selected image or video files;
prompt the user to enter identifying information pertaining to the one or more selected image or video files;
receive a selection of customization information, including one or more of music, a border, and identifying information, from the user;
create a customized video based on the selected one or more image or video files; and
format the customized video based on the user entered customization and identifying information.

12. The apparatus of claim 11, wherein the DICOM server providing the user access across the data network to the source set of image or video files includes providing access to at least one video clip and an image.

13. The apparatus of claim 11, wherein the processor is further configured to provide the customized video for download to the user's device across the data network.

14. The apparatus of claim 11, wherein the processor is being configured to receive the selection of customization information of one or more of a border and music to accompany the selected image or video files comprises the processor being configured to:
prompt the user to select between a) uploading to the DICOM server a choice of one or more of a border and music to accompany the image or video files and b) selecting from choices presented by the server of one or more of a border and music to accompany the selected image or video files, wherein
if the user selected to upload a choice of one or more of a border and music, accepting such an upload; and
if the user selected from choices presented by the server of one or more of a border and music, accepting the selection made by the user.

15. The apparatus of claim 11, wherein the processor is further configured to:
prompt the user to upload text to append to the image or video files;
accept text information uploaded by the user in response to the prompt; and
create the customized video including the text information.

16. The apparatus of claim 11, wherein the identifying information includes biographical information about a baby and at least one of its parents.

17. The apparatus of claim 11, wherein the processor is further configured to:
accept meta-data from the user across the data network; and
append the meta-data to the customized video.

18. The apparatus of claim 11, wherein the processor is further configured to:
accept at least one annotation, an audio overlay, and a diagram from the user across the data network; and
append the at least one annotation, audio overlay, and diagram to the customized video.

19. The apparatus of claim 11, wherein processor is further configured to select one or more advertisements to be displayed during creation of the customized video.

20. A computer readable medium encoded thereon with instructions that when executed cause a first apparatus to perform a method of wireless communication, the method comprising:
providing an interface to a user for accessing a DICOM server from a user's device over a data network;
receiving a source set of fetal ultrasound image or fetal ultrasound video files in a DICOM format from a network connected ultrasound equipment at the DICOM server coupled to the data network, the DICOM server comprising a processor and a memory that stores the user's credentials and associated images or video files;
provide the user access to the source set of image or video files on the DICOM server in response to receiving and validating user credentials;
select one or more image or video files from the source set of image or video files based on at least one of a user input or a medical office input;
prompt the user to select a plurality of different categories of customization information to accompany the one or more selected image or video files;
prompt the user to enter identifying information into the server;
receive a selection of customization information, including one or more of music and a border, and identifying information, from the user;
create a customized video based on the selected one or more image or video files; and format the customized video based on the user entered customization and identifying information.

* * * * *